(12) United States Patent
Kato et al.

(10) Patent No.: US 8,067,205 B2
(45) Date of Patent: Nov. 29, 2011

(54) METHOD OF SYNTHESIZING CDNA

(75) Inventors: Seishi Kato, Kanagawa (JP); Tomoko Kimura, Kanagawa (JP); Kuniyo Ohtoko, Ibaraki (JP)

(73) Assignees: Japan as represented by Director General of National Rehabilitation Center for Persons with Disabilities, Saitama (JP); Hitachi High-Technologies Corporation, Tokyo (JP); Sieshi Kato, Kanagawa (JP)

( * ) Notice: Subject to any disclaimer, the term of this patent is extended or adjusted under 35 U.S.C. 154(b) by 185 days.

(21) Appl. No.: 10/550,788

(22) PCT Filed: Mar. 29, 2004

(86) PCT No.: PCT/JP2004/004458
§ 371 (c)(1),
(2), (4) Date: Nov. 16, 2005

(87) PCT Pub. No.: WO2004/087916
PCT Pub. Date: Oct. 14, 2004

(65) Prior Publication Data
US 2006/0246453 A1    Nov. 2, 2006

(30) Foreign Application Priority Data
Mar. 28, 2003    (JP) .................................. 2003-091373

(51) Int. Cl.
*C12P 19/34*    (2006.01)
(52) U.S. Cl. ...................................................... 435/91.2
(58) Field of Classification Search ........................ 435/6
See application file for complete search history.

(56) References Cited

U.S. PATENT DOCUMENTS 5,597,713 A * 1/1997 Kato et al. .................. 435/91.41
5,962,271 A * 10/1999 Chenchik et al. ............ 435/91.1
6,352,829 B1 * 3/2002 Chenchik et al. .................. 435/6
6,368,802 B1 * 4/2002 Kool ................................. 435/6
6,558,927 B1 * 5/2003 Mueller et al. ............... 435/91.1

OTHER PUBLICATIONS

Shepard and Rae, Nucleic acids research, vol. 25, No. 15, pp. 3183-3185, 1997.*
Brennan et al. Methods in Enzymology, vol. 100, pp. 38-52, 1983.*
Suzuki et al., "Construction and Characterization of a Full Length-Enriched and a 5'-End-Enriched cDNA Library," Gene, vol. 200 (1997), pp. 149-156.
Okayama et al., "High-Efficiency Cloning of Full-Length cDNA," Molecular and Cellular Biology, vol. 2, No. 2 (1982), pp. 161-170.
Pruitt, S.C., "Expression Vectors Permitting cDNA Cloning and Enrichment for Specific Sequences by Hybridization/Selection," Gene, vol. 66 (1988), pp. 121-134.
Kato et al., "Construction of a Human Full-Length cDNA Bank," Gene, vol. 150 (1994), pp. 243-250.
Maruyama et al., "Oligo-Capping: A Simple Method to Replace the Cap Structure of Eukaryotic mRNAs with oligoribonucleotides," Gene, vol. 138 (1994), pp. 171-174.

* cited by examiner

*Primary Examiner* — Gary Benzion
*Assistant Examiner* — Cynthia Wilder
(74) *Attorney, Agent, or Firm* — Wenderoth, Lind & Ponack, L.L.P.

(57) ABSTRACT

A method for synthesizing cDNA possessing a consecutive sequence starting with a nucleotide adjacent to a cap structure of mRNA, which comprises (i) a process for annealing a double-stranded DNA primer and an RNA mixture containing mRNA possessing a cap structure, (ii) a process for preparing a conjugate of an mRNA/cDNA heteroduplex and a double-stranded DNA primer by synthesizing the first-strand cDNA primed with the double-stranded DNA primer using reverse transcriptase, and (iii) a process for circularizing the conjugate of the mRNA/cDNA heteroduplex and the double-stranded DNA primer by joining the 3' and 5' ends of the DNA strand containing cDNA using ligase. This method enables us to efficiently synthesize a full-length cDNA possessing a consecutive sequence starting with a transcription-start-site nucleotide from a small amount of RNA by small processes.

6 Claims, 4 Drawing Sheets

(dT tail of about 60 nucleotides)

Fig. 3

(A) pGCAP1

(B) pGCAP1 vector primer

(dT tail of about 60 nucleotides)

Fig. 4

(A) pGCAP10

(B) pGCAP10 vector primer (dT tail of about 60 nucleotides)

SEQUENCE LISTING

<160> NUMBER OF SEQ ID NOS: 2

<210> SEQ ID NO 1
<211> LENGTH: 3347
<212> TYPE: DNA
<213> ORGANISM: Artificial
<220> FEATURE:
<223> OTHER INFORMATION: pGCAP1: Modified from expression vector pKA1
<220> FEATURE:
<221> NAME/KEY: misc_feature
<223> OTHER INFORMATION: Circular polynucleotide

<400> SEQUENCE: 1

```
aagcttggct gtggaatgtg tgtcagttag ggtgtggaaa gtccccaggc tccccagcag      60
gcagaagtat gcaaagcatg catctcaatt agtcagcaac caggtgtgga aagtcccag     120 gctccccagc aggcagaagt atgcaaagca tgcatctcaa ttagtcagca accatagtcc    180
cgcccctaac tccgcccatc ccgccccctaa ctccgcccag ttccgcccat tctccgcccc   240
atggctgact aatttttttt atttatgcag aggccgaggc cgcctcggcc tctgagctat    300
tccagaagta gtgaggaggc ttttttggag gcctaggctt tgcaaaaag ctcctcgagg     360 aactgaaaaa ccagaaagtt aactggtaag tttagtcttt ttgtcttta tttcaggtcc    420 cggatccggt ggtggtgcaa atcaaagaac tgctcctcag tggatgttgc ctttacttct    480
aggcctgtac ggaagtgtta cttctgctct aaaagctgct cgagtgtaaa acgacggcca    540
gtacgtattt aatacgactc actataggga attccttaag atttaaatgt ggtaccgcgg    600
ccgcggatct cccttagtg agggttaatt ggatccagac atgataagat acattgatga    660
gtttggacaa accacaacta gaatgcagtg aaaaaaatgc tttattgtg aaatttgtga    720 tgctattgct ttatttgtaa ccattataag ctgcaataaa caagttaaca acaacaattg   780
cattcatttt atgtttcagg ttcaggggga ggtgtgggag gttttttctg cattaatgaa    840
tcggccaacg cgcggggaga ggcggtttgc gtattgggcg ctcttccgct tcctcgctca    900
ctgactcgct gcgctcggtc gttcggctgc ggcgagcggt atcagctcac tcaaaggcgg    960
taatacggtt atccacagaa tcaggggata acgcaggaaa gaacatgtga gcaaaaggcc   1020
agcaaaaggc caggaaccgt aaaaaggccg cgttgctggc gtttttccat aggctccgcc   1080 ccccctgacga gcatcacaaa aatcgacgct caagtcagag gtggcgaaac ccgacaggac   1140
tataaagata ccaggcgttt ccccctggaa gctccctcgt gcgctctcct gttccgaccc   1200
tgccgcttac cggatacctg tccgcctttc tcccttcggg aagcgtggcg ctttctcata   1260
gctcacgctg taggtatctc agttcggtgt aggtcgttcg ctccaagctg ggctgtgtgc   1320
acgaaccccc cgttcagccc gaccgctgcg ccttatccgg taactatcgt cttgagtcca   1380
acccggtaag acacgactta tcgccactgg cagcagccac tggtaacagg attagcagag   1440
cgaggtatgt aggcggtgct acagagttct tgaagtggtg gcctaactac ggctacacta   1500
gaaggacagt atttggtatc tgcgctctgc tgaagccagt taccttcgga aaaagagttg   1560
gtagctcttg atccggcaaa caaaccaccg ctggtagcgg tggttttttt gtttgcaagc   1620
agcagattac gcgcagaaaa aaaggatctc aagaagatcc tttgatcttt tctacggggt    1680
ctgacgctca gtggaacgaa aactcacgtt aagggatttt ggtcatgaga ttatcaaaaa   1740
ggatcttcac ctagatcctt ttaaattaaa aatgaagttt taaatcaatc taaagtatat   1800
atgagtaaac ttggtctgac agttaccaat gcttaatcag tgaggcacct atctcagcga   1860
tctgtctatt tcgttcatcc atagttgcct gactccccgt cgtgtagata actacgatac   1920
```

```
gggagggctt accatctggc cccagtgctg caatgatacc gcgagaccca cgctcaccgg    1980
ctccagattt atcagcaata aaccagccag ccggaagggc cgagcgcaga agtggtcctg    2040
caactttatc cgcctccatc cagtctatta attgttgccg ggaagctaga gtaagtagtt    2100
cgccagttaa tagtttgcgc aacgttgttg ccattgctac aggcatcgtg gtgtcacgct    2160
cgtcgtttgg tatggcttca ttcagctccg gttcccaacg atcaaggcga gttacatgat    2220
cccccatgtt gtgcaaaaaa gcggttagct ccttcggtcc tccgatcgtt gtcagaagta    2280
agttggccgc agtgttatca ctcatggtta tggcagcact gcataattct cttactgtca    2340
tgccatccgt aagatgcttt tctgtgactg gtgagtactc aaccaagtca ttctgagaat    2400
agtgtatgcg gcgaccgagt tgctcttgcc cggcgtcaat acgggataat accgcgccac    2460
atagcagaac tttaaaagtg ctcatcattg gaaaacgttc ttcggggcga aaactctcaa    2520
ggatcttacc gctgttgaga tccagttcga tgtaacccac tcgtgcaccc aactgatctt    2580
cagcatcttt tactttcacc agcgtttctg gtgagcaaa acaggaagg caaaatgccg    2640 caaaaaggg aataagggcg acacggaaat gttgaatact catactcttc ctttttcaat    2700
attattgaag catttatcag ggttattgtc tcatgagcgg atacatattt gaatgtattt    2760
agaaaaataa acaaataggg gttccgcgca catttccccg aaaagtgcca cctgaaattg    2820
taaacgttaa tattttgtta aaattcgcgt taaattttg ttaaatcagc tcatttttta    2880
accaataggc cgaaatcggc aaaatccctt ataaatcaaa agaatagacc gagatagggt    2940
tgagtgttgt tccagtttgg aacaagagtc cactattaaa gaacgtggac tccaacgtca    3000
aagggcgaaa aaccgtctat cagggcgatg gcccactacg tgaaccatca ccctaatcaa    3060
gttttttggg gtcgaggtgc cgtaaagcac taaatcggaa ccctaaaggg agccccgat    3120 ttagagcttg acggggaaag ccggcgaacg tggcgagaaa ggaagggaag aaagcgaaag    3180
gagcgggcgc tagggcgctg gcaagtgtag cggtcacgct gcgcgtaacc accacacccg    3240
ccgcgcttaa tgcgccgcta cagggcgcgt cccattcgcc attcacacag gaaacagcta    3300
tgaccatgat cctctagagt cgacctgcag gcatgcttaa ttaaggg                 3347
```

<210> SEQ ID NO 2
<211> LENGTH: 3357
<212> TYPE: DNA
<213> ORGANISM: Artificial
<220> FEATURE:
<223> OTHER INFORMATION: pGCAP10: Modified from pGCAP1 of SEQ ID No. 1
<220> FEATURE:
<221> NAME/KEY: misc_feature
<223> OTHER INFORMATION: Circular polynucleotide

<400> SEQUENCE: 2

```
aagcttggct gtggaatgtg tgtcagttag ggtgtggaaa gtccccaggc tccccagcag      60
gcagaagtat gcaaagcatg catctcaatt agtcagcaac caggtgtgga aagtccccag     120
gctccccagc aggcagaagt atgcaaagca tgcatctcaa ttagtcagca accatagtcc     180
cgcccctaac tccgcccatc ccgcccctaa ctccgcccag ttccgcccat tctccgcccc     240
atggctgact aatttttttt atttatgcag aggccgaggc cgcctcggcc tctgagctat     300
tccagaagta gtgaggaggc ttttttggag gcctaggctt tgcaaaaag ctcctcgagg     360 aactgaaaaa ccagaaagtt aactggtaag tttagtcttt ttgtcttta tttcaggtcc     420 cggatccggt ggtggtgcaa atcaaagaac tgctcctcag tggatgttgc ctttacttct     480
aggcctgtac ggaagtgtta cttctgctct aaaagctgct cgagtgtaaa acgacggcca     540
```

```
gtacgtattt aatacgactc actataggga atttaaatga attcggccgg ccgatatcct    600
ggtaccgcgg ccgcggatct ccctttagtg agggttaatt ggatccagac atgataagat    660
acattgatga gtttggacaa accacaacta gaatgcagtg aaaaaaatgc tttatttgtg    720
aaatttgtga tgctattgct ttatttgtaa ccattataag ctgcaataaa caagttaaca    780
acaacaattg cattcatttt atgtttcagg ttcaggggga ggtgtgggag gttttttctg    840
cattaatgaa tcggccaacg cgcggggaga ggcggtttgc gtattgggcg ctcttccgct    900
tcctcgctca ctgactcgct gcgctcggtc gttcggctgc ggcgagcggt atcagctcac    960
tcaaaggcgg taatacggtt atccacagaa tcaggggata cgcaggaaa gaacatgtga   1020
gcaaaaggcc agcaaaaggc caggaaccgt aaaaaggccg cgttgctggc gttttccat   1080
aggctccgcc cccctgacga gcatcacaaa aatcgacgct caagtcagag gtggcgaaac   1140
ccgacaggac tataaagata ccaggcgttt ccccctggaa gctccctcgt gcgctctcct   1200
gttccgaccc tgccgcttac cggatacctg tccgcctttc tcccttcggg aagcgtggcg   1260
ctttctcata gctcacgctg taggtatctc agttcggtgt aggtcgttcg ctccaagctg   1320
ggctgtgtgc acgaaccccc cgttcagccc gaccgctgcg ccttatccgg taactatcgt   1380
cttgagtcca acccggtaag acacgactta tcgccactgg cagcagccac tggtaacagg   1440
attagcagag cgaggtatgt aggcggtgct acagagttct tgaagtggtg cctaactac   1500
ggctacacta gaaggacagt atttggtatc tgcgctctgc tgaagccagt taccttcgga   1560
aaaagagttg gtagctcttg atccggcaaa caaaccaccg ctggtagcgg tggtttttttt   1620
gtttgcaagc agcagattac gcgcagaaaa aaaggatctc aagaagatcc tttgatcttt   1680
tctacggggt ctgacgctca gtggaacgaa aactcacgtt aagggatttt ggtcatgaga   1740
ttatcaaaaa ggatcttcac ctagatcctt ttaaattaaa aatgaagttt taaatcaatc   1800
taaagtatat atgagtaaac ttggtctgac agttaccaat gcttaatcag tgaggcacct   1860
atctcagcga tctgtctatt tcgttcatcc atagttgcct gactccccgt cgtgtagata   1920
actacgatac gggagggctt accatctggc cccagtgctg caatgatacc gcgagaccca   1980
cgctcaccgg ctccagattt atcagcaata aaccagccag ccggaagggc cgagcgcaga   2040
agtggtcctg caactttatc cgcctccatc cagtctatta attgttgccg ggaagctaga   2100
gtaagtagtt cgccagttaa tagtttgcgc aacgttgttg ccattgctac aggcatcgtg   2160
gtgtcacgct cgtcgtttgg tatggcttca ttcagctccg gttcccaacg atcaaggcga   2220
gttacatgat cccccatgtt gtgcaaaaaa gcggttagct ccttcggtcc tccgatcgtt   2280
gtcagaagta agttggccgc agtgttatca ctcatggtta tggcagcact gcataattct   2340
cttactgtca tgccatccgt aagatgcttt tctgtgactg gtgagtactc aaccaagtca   2400
ttctgagaat agtgtatgcg gcgaccgagt tgctcttgcc cggcgtcaat acgggataat   2460
accgcgccac atagcagaac tttaaaagtg ctcatcattg gaaaacgttc ttcggggcga   2520
aaactctcaa ggatcttacc gctgttgaga tccagttcga tgtaacccac tcgtgcaccc   2580
aactgatctt cagcatcttt tactttcacc agcgtttctg ggtgagcaaa aacaggaagg   2640
caaaatgccg caaaaaaggg aataagggcg acacggaaat gttgaatact catactcttc   2700
ctttttcaat attattgaag catttatcag ggttattgtc tcatgagcgg atacatattt   2760
gaatgtattt agaaaaataa acaaataggg gttccgcgca catttccccg aaaagtgcca   2820
cctgaaattg taaacgttaa tattttgtta aaattcgcgt taaattttg ttaaatcagc   2880
tcatttttta accaataggc cgaaatcggc aaaatccctt ataaatcaaa agaatagacc   2940
```

-continued

```
gagatagggt tgagtgttgt tccagtttgg aacaagagtc cactattaaa gaacgtggac    3000
tccaacgtca aagggcgaaa aaccgtctat cagggcgatg gcccactacg tgaaccatca    3060
ccctaatcaa gttttttggg gtcgaggtgc cgtaaagcac taaatcggaa ccctaaaggg    3120
agcccccgat ttagagcttg acggggaaag ccggcgaacg tggcgagaaa ggaagggaag    3180
aaagcgaaag gagcgggcgc tagggcgctg gcaagtgtag cggtcacgct gcgcgtaacc    3240
accacacccg ccgcgcttaa tgcgccgcta cagggcgcgt cccattcgcc attcacacag    3300
gaaacagcta tgaccatgat cctctagagt cgacctgcag gcatgcttaa ttaaggg      3357
```

METHOD OF SYNTHESIZING CDNA

This application is a U.S. national stage of International Application No. PCT/JP2004/004458 filed Mar. 29, 2004.

TECHNICAL FIELD

The invention of this application relates to a method of cDNA synthesis. More particularly, the invention of this application relates to a novel, simple and high-efficient method for synthesizing cDNA possessing a consecutive sequence starting with a nucleotide adjacent to a cap structure of mRNA.

BACKGROUND ART

Genome projects have determined almost all sequences of genome DNA (chromosome DNA) that covers all genetic information of various organisms including human, mouse, rice, nematoda, yeast and so on. The entire sequence of these genomes is expected to give us information on the primary structure of proteins encoded by genes and information on the expression regulation regions (promoter, enhancer, suppressor etc.) that regulate the expression of the gene. In order to extract these two kinds of information from the genome sequence, the sequence information of mRNA transcribed from the gene locus of chromosome DNA is crucial. In order to analyze the sequence of mRNA, DNA complementary to mRNA (complementary DNA: cDNA) has been usually used. Especially, in order to obtain the foregoing two kinds of information, it is necessary to obtain cDNA (full-length cDNA) synthesized from mRNA that is correctly transcribed from the gene transcription region and contains an entire protein-coding region.

Usually, full-length cDNA must meet two requirements. One is to possess a sequence starting with a transcription start site on the genome DNA. A "cap structure" is added to the 5' end of mRNA that is properly transcribed from the transcription start site. This cap structure is 7-methylguanosin ($m^7G$) connected to the transcription-start-site nucleotide via 5'-5' triphosphate linkage. The cDNA complementary to the mRNA possessing this cap structure meets one requirement for full-length cDNA. Another indicator is the presence of a "poly(A) tail" of mRNA. This poly(A) tail is a consecutive sequence of several ten to 200 adenines (A) that is added to the 3' end of mRNA in the nucleus after transcription of genome DNA. Therefore, cDNA correctly synthesized from a mRNA template possessing both the cap structure at the 5' end and the poly(A) tail at the 3' end meets the two requirements for full-length cDNA (starting with a transcription start site and encompassing an entire protein-coding region).

The cDNA can be synthesized by reverse transcriptase reaction using mRNA as a template, but it is difficult to synthesize full-length cDNA, because mRNA transcribed from chromosome DNA is exposed to various degradation reactions in cells or during an extraction process from cells or during a synthesis process to a DNA strand. The reverse transcription reaction using mRNA as a template synthesizes a DNA strand (the first-strand cDNA) toward the 5' direction of mRNA from a primer oligonucleotide that is annealed with the 3' end of mRNA. Thus, when the primer (oligo dT) is annealed with a poly(A) tail, it is easy to obtain cDNA covering the poly(A) tail. However, this method does not guarantee the synthesis of full-length cDNA possessing a sequence encompassing from the primer to the cap structure, because degradation of mRNA and/or interruption of synthesis reaction of the DNA strand frequently occur. In fact, most of a vast number of ESTs (expressed sequence tag) reported so far were derived from incomplete cDNAs generated from degraded mRNA or incomplete cDNAs generated by interruption of synthesis reaction of the DNA strand.

Therefore, many methods have been proposed to synthesize full-length cDNA possessing a sequence encompassing to the cap structure that exists at the 5' end of mRNA. These methods are classified into the following four main cases based on the used principle.

(1) Tailing Method

This method is based on the addition of a homo-oligomer tail using terminal transferase to the first-strand cDNA extended to the cap structure. The Okayama-Berg method (Non-patent Document 1) and the Pruitt method (Non-patent Document 2) are included in this category. Since it is difficult to strictly control the number of the added tail, this method has a problem that too long tailing makes nucleotide sequence analysis difficult.

The template-switching method (Patent Document 1), that uses a dC tail added to the 3' end of the first-strand cDNA by the terminal transferase activity of reverse transcriptase, is also included in this tailing method. The number of added dC was described to be 3 to 5 in the reference (Non-patent Document 3).

(2) Linker-ligation Method

This method comprises synthesis of the first-strand cDNA, removal of mRNA by alkaline or RNase H treatment, and ligation of a single-stranded oligonucleotide linker with known sequence to the 3' end of the single-stranded cDNA using T4 RNA ligase (Non-patent Document 4). This method is inappropriate to prepare a high-quality cDNA library because of formation of the secondary structure in the single-stranded cDNA.

(3) Oligo-capping Method

This method is based on the replacement of the cap structure with an oligomer. The methods using an RNA oligomer (Non-patent Document 5) or a DNA-RNA chimeric oligomer (for example, Patent Document 1 by inventors of this application, Non-patent Document 6) have been reported. This method should produce only full-length cDNAs in principle, but also produces some truncated cDNAs synthesized from degraded mRNAs that are produced during many processes for treating mRNA, and besides a lot of poly(A)$^+$ RNA of about 5-10 µg is necessary. The use of total RNA as a starting material to suppress the degradation of mRNA has been reported to improve the full-length rate to be more than 90%, but the number of reaction steps unchanged (Patent Document 3).

This method includes the method (Patent Document 3) in which a synthetic oligomer was added to the cap structure after opening its carbohydrate ring by periodate oxidation reaction.

(4) Cap-trapping Method

This method is based on selecting mRNAs possessing a cap structure and using them as a template. It includes the method using mRNA selected by anti-cap antibody as a template (Non-patent Document 7) and the method using biotinylated mRNA that is prepared by adding biotin to an open ring generated by periodate oxidation of the carbohydrate of the cap structure and selecting by avidin-immobilized carrier (Non-patent Document 8).

Patent Document 1: U.S. Pat. No. 5,962,272
Patent Document 2: 3337748
Patent Document 3: WO 01/04286
Patent Document 4: U.S. Pat. No. 6,022,715
Non-patent Document 1: Okayama, H. and Berg, P. Mol. Cell. Biol. 2:161-170, 1982.

Non-patent Document 2: Pruitt, S. C. Gene 66:121-134, 1988.

Non-patent Document 3: CLONTECHniques, July 1997, p. 26.

Non-patent Document 4: Edwards, J., Delort, J., and Mallet, J. Nucleic Acids Res. 19:5227-5232, 1991.

Non-patent Document 5: Maruyama, K. and Sugano, S. Gene 138:171-174, 1994.

Non-patent Document 6: Kato et al., Gene 150:243-250, 1994. Non-patent Document 7: Edery, I., Chu, L. L., Sonenberg, N., and Pelletier, J. Mol. Cell. Biol. 15:3363-3371, 1995.

Non-patent Document 8: Caminci et al., Genomics 37:327-336, 1996.

DISCLOSURE OF INVENTION

The forgoing any conventional method enables us to synthesize full-length cDNA. However, even if synthesized cDNAs contains full-length cDNA at high rates, they inevitably include incomplete cDNAs derived from degraded mRNA and/or incomplete cDNAs produced by interruption of cDNA synthesis. Therefore, it is necessary to determine whether or not the synthesized cDNA is derived from full-length mRNA possessing a cap structure. In general, if multiple clones possessing the same 5'-teminal sequence exist, it is highly possible that these clones are derived from full-length mRNA, but not conclusive. Especially, in the case of genes possessing multiple transcription start sites, it is very difficult to determine whether the cDNA clone is derived from full-length mRNA or from degraded mRNA lacking a 5' end.

Therefore, a method for synthesizing cDNA, by which we can synthesize full-length cDNA at high rates and determine whether or not it possesses a sequence starting with a transcription start site, has been desired.

Also, the foregoing any conventional method has a problem that they require many processes. For example, the oligo-capping method described in Patent Document 1 is superior with respect to its ability to certainly synthesize cDNA possessing a nucleotide sequence starting with a cap site, but it requires 8 processes to synthesize cDNA. The increase of processes causes problems such as the decrease of synthetic yield and the increases of time, labor, and cost.

Furthermore, some conventional methods contain an amplification process by PCR (Non-patent Documents 4 and 5). Thus, these methods had a problem that the generated cDNA sequence had artificial mutations because DNA polymerase used for PCR frequently incorporated a nucleotide different from the template nucleotide during polymerase reaction.

Therefore, a method for synthesizing full-length cDNA from a low amount of RNA by small processes without using PCR has been desired.

The invention of this application has done under the foregoing circumstances, and makes it an object to provide a cDNA synthesis method satisfying the following requirements:

(1) a starting material is total RNA of one to several micrograms;
(2) no use of PCR;
(3) to consist of as small processes as possible;
(4) to synthesize full-length cDNA that is guaranteed to possess a consecutive sequence starting with a transcription-start-site nucleotide in a high yield of more than 90%.

No conventional method satisfies all of these requirements.

The first invention to solve the foregoing subject is a method for synthesizing cDNA possessing a consecutive sequence starting with a nucleotide adjacent to a cap structure of mRNA, which method comprises the processes of:

(i) annealing a double-stranded DNA primer and an RNA mixture containing mRNA possessing a cap structure,
(ii) preparing a conjugate of an mRNA/cDNA heteroduplex and the double-stranded DNA primer by synthesizing the first-strand cDNA primed with the double-stranded DNA primer using reverse transcriptase, and
(iii) circularizing the conjugate of the mRNA/cDNA heteroduplex and the double-stranded DNA primer by joining the 3' and 5' ends of the DNA strand containing cDNA using ligase.

In the method of this first invention, a preferred aspect is that mRNA possessing a cap structure is contained in a cell extract, or that mRNA possessing a cap structure is synthesized by in vitro transcription.

Also, in the method of this first invention, a preferred aspect is that the primer sequence of the double-stranded DNA primer contains a sequence complementary to a partial sequence of mRNA possessing a cap structure or an oligo dT complementary to a poly(A) sequence of mRNA possessing a cap structure.

Furthermore, in the method of this first invention, a preferred aspect is that the ligase is T4 RNA ligase.

In the method of this first invention, another preferred aspect is that it comprises the following process between the processes (ii) and (iii),:

(ii') generating a 5'-protruding end or a blunt end at the terminal of the double-stranded DNA primer by cutting the conjugate of the mRNA/cDNA heteroduplex and the double-stranded DNA primer using a restriction enzyme.

The second invention is a method for synthesizing cDNA, which comprises the following process in addition to the method of the foregoing first invention:

(iv) synthesizing a second-strand cDNA by replacing an RNA strand with a DNA strand in the conjugate of the mRNA/cDNA heteroduplex and the double-stranded DNA primer.

In the method of this second invention, a preferred aspect is that the double-stranded DNA primer contains a replication origin or both a replication origin and a promoter for cDNA expression.

The method of this second invention provides a clone containing the synthesized double-stranded cDNA.

In the method of this second invention, another preferred aspect is to include the following process for:

(v) incorporating the double-stranded cDNA composed of the first-strand cDNA and the second-strand cDNA into a vector DNA.

This process enables us to clone the synthesized double-stranded cDNA into a vector.

The third invention is a cDNA library that is a population of clones containing double-stranded cDNA synthesized by the method of the foregoing second invention, of which more than 60% of the cDNA clones possesses a 5'-end nucleotide of (dT)ndG (n=0-5) followed by a consecutive sequence starting with a nucleotide adjacent to a cap structure of mRNA.

The forth invention is a method for selecting a cDNA clone possessing a consecutive sequence starting with a nucleotide adjacent to a cap structure of mRNA, from clones in the cDNA library of the forgoing third invention, wherein a cDNA clone possessing a 5'-end nucleotide of (dT)ndG (n=0-5) is selected as an objective clone.

The fifth invention is a double-stranded DNA primer possessing an oligo (dT)n (n=15-100) as a primer part, in which one terminal part of a primer side has an 8-base recognition restriction enzyme site RE1, and another terminal part has an 8-base recognition restriction enzyme site RE2 and a restriction enzyme site RE3 generating a 5'-protruding end or a blunt end.

A preferred aspect of the fifth invention is that a double-stranded DNA primer contains a replication origin or both a replication origin and a promoter for cDNA expression. An example of the double-stranded DNA primer of the fifth invention is a vector primer derived from pGCAP10 comprising the nucleotide sequence of SEQ ID NO: 2.

The sixth invention is a reagent kit for cDNA synthesis, which comprises a double-stranded DNA primer, reverse transcriptase and its reaction buffer solution, T4 RNA ligase and its reaction buffer solution, and model mRNA possessing a cap structure.

The foregoing invention is a method for synthesizing cDNA possessing a consecutive sequence starting with a nucleotide adjacent to a cap structure of mRNA in high yield, which method comprises at least the following three processes:
(i) annealing of a double-stranded primer and mRNA,
(ii) preparation of a conjugate of a mRNA/cDNA heteroduplex and the double-stranded DNA primer by synthesizing the first-strand cDNA,
(iii) joining the 3' and 5' ends of a DNA strand containing cDNA in the conjugate of the mRNA/cDNA heteroduplex and the double-stranded DNA primer.

This invention has been completed by finding that, when mRNA possessing a cap structure was used as a template and the base of the cap was "G", "dC" [or 5'-dC(dA)n-3' (n=1-5)] was added to the 3' end of the first-strand cDNA by the foregoing process (ii). Since "dT" [or 5'-dT(dA)n-3' (n=1-5)] was added to the 3' end of the first-strand cDNA when the base of the cap was "A", the added nucleotide was shown to have the base complementary to that of the cap structure. Also, no addition of an extra nucleotide to the 3' end of the first-strand cDNA was observed when RNA not possessing a cap structure was used as a template. Thus, when extra "dG" [or 5'-dG(dT)n-3' (n=1-5)] exists at the 5' end of the cDNA, we can decide that this cDNA is full-length cDNA derived from mRNA possessing a cap structure. Since more than one extra "dG" can be added depending on reaction conditions of reverse transcriptase (non-patent reference), if (dN)ndG (dN is dT or dG, n=0-5) exists at the 5' end of the cDNA, generally we can decide that this cDNA is full-length cDNA derived from mRNA possessing a cap structure. However, when more than one extra "dG" are added, it is difficult to decide which "dG" is extra one. Thus, it is preferable to be performed under conditions for adding one extra "dG" as shown in Examples.

In addition, the addition of 3-5 dCs was described in the template-switching method (non-patent reference 3), but we could not observe such addition of multiple dCs under conditions in Examples of this invention. Also, there is a report that one dC was preferentially added to the 3' end of the first-strand cDNA by terminal transferase-like activity of reverse transferase (Schmidt, W. M. and Muller, M. W., Nucleic Acids Res. 27:e31, 1999), but there is no report about its mechanism. Furthermore, there is a report that, when reverse transcriptase acted on an RNA/DNA heteroduplex (corresponding to the cap structure-free RNA/DNA heteroduplex in this invention), one nucleotide ("dA" or "dG" or "dC" or "dT") was added to 90% of the 3' end of DNA (Chen, D. and Patton, J. T., BioTechniques 30:574-582, 2001), but such addition was seldom observed under conditions in Examples of this invention.

In this invention, the term "nucleotide" means phosphoester (ATP, CTP, CTP, UTP; or dATP, dGTP, dCTP, dTTP) of nucleoside that contains a sugar linked to purine or pyrimidine via a beta-N-glycosidic bond. Hereafter these nucleotides can be described simply by "A", "G", "C", "U", or "dA", "dG", or "dC", "dT". The term "complementary" means a pairing of the nucleotides via a hydrogen bond; "A" (or "dA") and "U" (or "dr"), or "G" (or "dG") and "C" (or "dC").

The term "double-stranded DNA primer" means double-stranded DNA in which one end of a DNA strand is a 3'-protruding end whose sequence is complementary to that of template mRNA. This protruding part hybridizes the template mRNA, and works as a primer for the first-strand cDNA synthesis by reverse transcriptase. In particular, double-stranded DNA with a replication origin is called a "vector primer".

Furthermore, in this invention, the term "mRNA possessing a cap structure" means mRNA that is transcribed from genome DNA and whose 5' end is linked by guanosine possessing methylated guanine (G) via a 5'-5' triphosphate bond (mGp5'-5'pp). For example, in the case of a cap structure in which the seventh position of G is methylated, the mRNA has the following structure:

5'-m$^7$GN$_1$N$_2$N$_3$N$_4$N$_5$ - - - N$_m$-3':  (a)

(where N is A, G, C, or U, and m is a positive number of more than 50)

In this invention, the term "cDNA possessing a consecutive sequence starting with a nucleotide adjacent to a cap structure of mRNA" means all cDNAs including the following cDNAs. cDNA (the first-strand cDNA) complementary to a sequence N$_1$ - - - N$_m$ in the foregoing structure (a) of mRNA, wherein the 3' end is added by 5'-dC(dA)$_n$-3' (n=0-5) (in more general, 5'-dC(dN)$_n$-3' (where dN is dA or dC, n=0-5)):

3'-(dA)ndCdN$_1$dN$_2$dN$_3$dN$_4$dN$_5$ - - - dN$_m$-5':  (b)

(where dN is dA, dG, dC, or dT),
cDNA (the second-strand cDNA) complementary to this cDNA (b):

5'-(dT)ndGdN$_1$dN$_2$dN$_3$dN$_4$dN$_5$ - - - dN$_m$_3':  (c), and a cDNA (b)/(c) duplex (double-stranded cDNA). The term "cDNA" simply means double-stranded cDNA, but it means the second-strand cDNA described by the foregoing structure (c) in the case of referring to its sequence.

Since the N$_1$ in the structure (a) of mRNA is a nucleotide corresponding to a transcription start site, "cDNA possessing a consecutive sequence starting with a nucleotide adjacent to a cap structure of mRNA" can also be defined as "cDNA possessing a consecutive sequence starting with a transcription-start-site nucleotide".

Hereafter "cDNA possessing a consecutive nucleotide starting with a nucleotide (a transcription-start-site nucleotide) adjacent to a cap structure of mRNA" can be described as "cap-consecutive cDNA". Also, in particular, cap-consecutive cDNA possessing a poly(A) sequence can be described as "full-length cDNA". Furthermore, cDNA that does not contain a nucleotide (at least dN$_1$ in the structure (b) or (c)) adjacent to a cap structure can be described as "cap-nonconsecutive cDNA". Still furthermore, "mRNA possessing a cap structure" can be described as "cap(+)mRNA", "mRNA not possessing a cap structure" can be described as "cap(−)mRNA", and mRNA that is produced by removing a cap structure from cap(+)mRNA can be described as "decapped mRNA".

Other terms and concepts according to this invention will be defined in detail by referring to the embodiments of the invention and Examples. In addition, various techniques to be used for carrying out this invention can be easily and surely carried out by those skilled in the art on the basis of known literatures and the like except for the techniques whose references are particularly specified. For example, the techniques of genetic engineering and molecular biology of this invention are described in Sambrook and Maniatis, in Molecular Cloning—A laboratory Manual, Cold Spring Harbor Press, New York, 1989; Ausubel, F. M. et al., Current Protocols in Molecular Biology, John and Wiley & Sons, New York, N.Y. 1995, and the like.

BEST MODE FOR CARRYING OUT THE INVENTION

Figure 1:
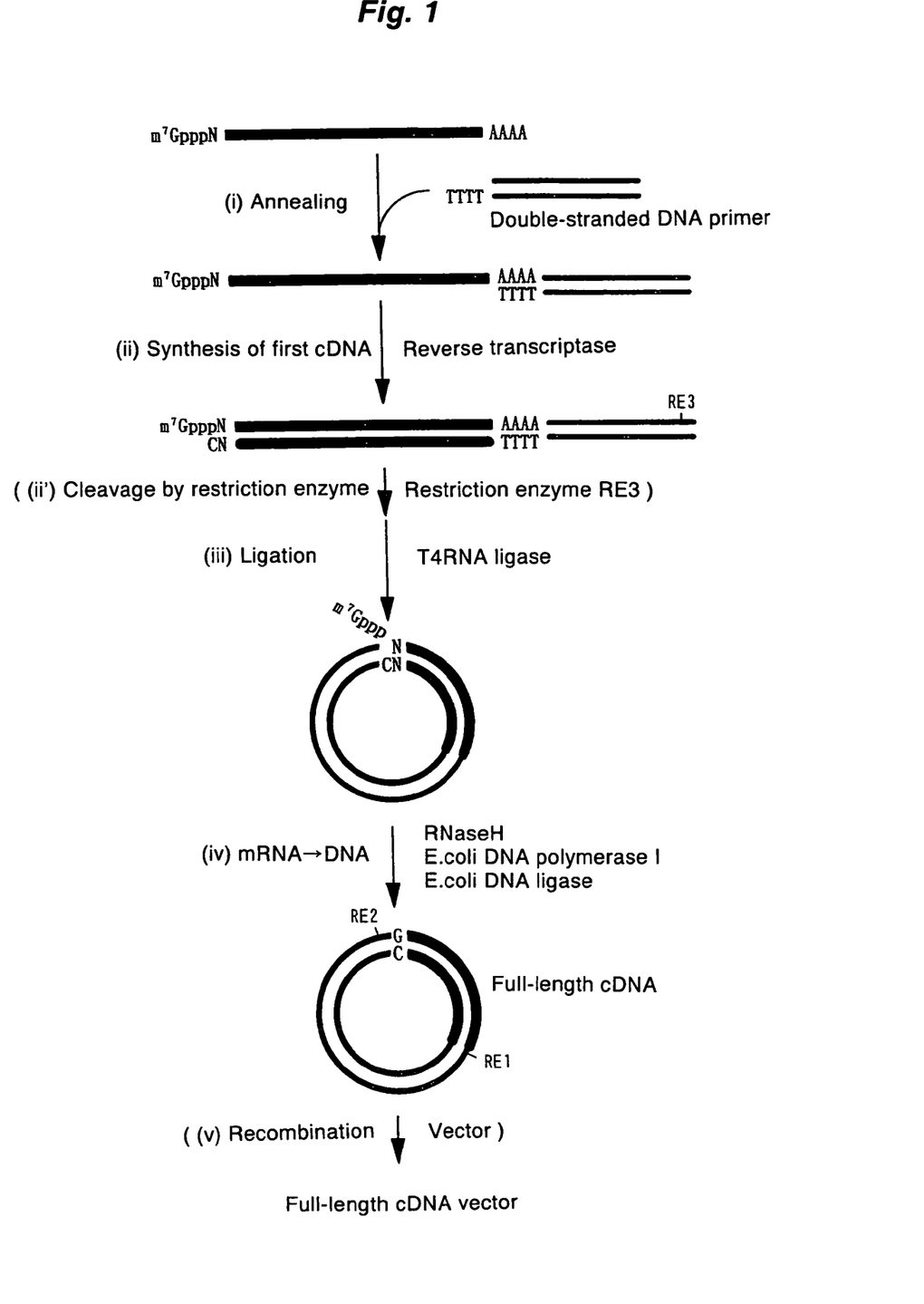
FIG. 1 is a diagram schematically showing basic processes of this invention.

The first invention is a method for synthesizing cap-consecutive cDNA (the first-strand cDNA), which method indispensably comprises the following processes (i), (ii), and (iii) (refer to FIG. 1).
Process (i): to anneal a double-stranded DNA primer and an RNA mixture containing mRNA possessing a cap structure.
Process (ii): to prepare a conjugate of an mRNA/cDNA heteroduplex and the double-stranded DNA primer by synthesizing the first-strand cDNA primed with the double-stranded DNA primer using reverse transcriptase.
Process (iii): to circularize the conjugate of the mRNA/cDNA heteroduplex and the double-stranded DNA primer by joining the 3' and 5' ends of the DNA strand containing cDNA using ligase.

In the process (i), an "RNA mixture containing mRNA possessing a cap structure" may contain either only mRNA possessing a cap structure or others such as "cap(–)mRNA" and/or "other RNA molecules (for example, rRNA, tRNA etc.)". Such an RNA mixture may be derived from either single cellular eukaryotes or multicellular eukaryotes. Also, this RNA mixture may be either RNA synthesized by in vitro transcription using DNA as a template or total RNA extracted from cells. In this process (i), although less than one μg of total RNA can be used as the RNA mixture to synthesize cDNA, more than one μg of total RNA is preferentially used. Although an mRNA content in total RNA extracted from cells is 2-3%, the method of this invention enables us to synthesize cap-consecutive cDNA or full-length cDNA from total RNA containing such a low amount of mRNA.

A "double-stranded DNA primer" used in the process (i) has a "primer sequence" at its 3'-protruding end. When information on the partial sequence of target mRNA possessing a cap is known, the primer sequence can be prepared based on this known sequence using known chemical synthetic methods (for example, methods described in Carruthers, Cold Spring Harbor Symp. Quant. Biol. 47:411-418, 1982; Adams, J. Am. Chem. Soc. 105:661, 1983; Belousov, Nucleic Acid Res. 25:3440-3444, 1997; Frenkel, Free Radic. Biol. Med. 19:373-380, 1995; Blommers, Biochemistry 33:7886-7896, 1994; Narang, Meth. Enzymol. 68:90, 1979; Brown, Meth. Enzymol. 68:109, 1979; Beaucage, Tetra. Lett. 22:1859, 1981; U.S. Pat. No. 4,458,066). Most of known EST (expressed sequence tag) sequences were derived from a 3'-end partial sequence of cDNA. Using a primer sequence prepared based on these EST sequences, we can obtain cap-consecutive cDNA containing the 5'-upstream region of the corresponding EST sequence. Also a primer containing an oligo dT that is complementary to poly(A) of mRNA can be used. The number of consecutive dT composed of the oligo dT is preferentially 30-70. Using these oligo dT primers, cap-consecutive cDNA encompassing to a poly(A) site (full-length cDNA) can be obtained. On the other hand, there is no restriction on the other terminal sequence of the double-stranded DNA primer so that any double-stranded DNA can be used, but preferentially it should possess a linking terminal for joining to the cloning site of a vector DNA to make it easy to insert into the vector DNA on the later process.

In the process (ii), by acting reverse transcriptase on the double-stranded DNA primer annealed with mRNA, a cDNA strand complementary to mRNA is synthesized in the 5' direction of mRNA starting from the 3' end of the double-stranded DNA primer. This process produces a conjugate of an mRNA/cDNA heteroduplex and a double-stranded DNA primer. In this conjugate, one end of the cDNA strand in the mRNA/cDNA heteroduplex joins the end of one strand in the double-stranded DNA primer. Furthermore, cDNA in the mRNA/cDNA heteroduplex produced by this process (ii) is cap-consecutive cDNA that is complementary to cap(+)mRNA and possesses dC or 5'-dC(dA)$_n$-3' at its 3' end, or cap-non-consecutive cDNA that is derived from cap(–)mRNA.

As reverse transcriptase, an enzyme that is derived from M-MLV (Moloney murine leukemia virus) or AMV (avian myeloblastosis virus) can be used, but endogenous RNaseH activity-removed one is preferable.

As ligase in this process (iii), various kinds of DNA ligase or RNA ligase of choice can be used, but T4 RNA ligase is preferable. There is a report on a method to join two oligodeoxynucleotides hybridized to RNA using T4 RNA ligase (U.S. Pat. No. 6,368,801), but there is no report on ligation between an mRNA/cDNA heteroduplex and a double-stranded DNA. The ligation is preferably performed after carrying out a process (ii') by which the end of the double-stranded DNA primer is converted to a 5'-protruding end or a blunt end by cutting the conjugate of the mRNA/cDNA heteroduplex and the double-stranded DNA with restriction enzyme. The disadvantage by this increase of one process is compensated by merits that are decrease of background composed of only vector without a cDNA insert and increase of ligation efficiency. The cap structure of the mRNA/cDNA heteroduplex may or may not be removed, for example, using tobacco acid pyrophosphatase. Furthermore the ligation may be performed after degradation of mRNA in the mRNA/cDNA or replacement of the mRNA strand by a DNA strand. In this case, it should be noted that the degradation product of mRNA generated during this process can be added to the 3' end of the cDNA.

The foregoing method enables us to synthesize a circular DNA strand that contains cap-consecutive cDNA (the first-strand cDNA) described by the following, 3'-(dA)ndCdN$_1$dN$_2$dN$_3$dN$_4$dN$_5$ - - - Nm-5':     (b)

The obtained cap-consecutive cDNA provides information to specify a transcription start site of a gene and an expression regulation region at its upstream by analyzing the sequence of the cDNA and comparing it with a genome sequence.

The cap-consecutive cDNA (the first-strand cDNA) obtained using the foregoing method is converted to double-stranded cDNA by the process (iv) of the second invention. This process (iv) can be performed by replacing an RNA strand with a DNA strand, for example, by acting RNaseH, *E. coli* DNA polymerase I, *E. coli* DNA ligase, and the like. This process is not necessary to be done in vitro; for example, if a "vector primer" is used as a double-stranded DNA primer, the RNA strand can be replaced with the DNA strand in cells such as *E. coli* cells after the ligation product is introduced into the cells.

The method of the second invention enables us to clone the double-stranded cDNA into a vector by the process (v). For example, after cutting with restriction enzyme sites that are set up in the double-stranded DNA, the double-stranded cDNA can be inserted into a plasmid vector or phage vector, and then used for sequencing analysis or production of its expression product.

In the method of this second invention, the use of a "vector primer" as a double-stranded DNA primer is preferable because the process for inserting the cDNA into other vector can be omitted. The vector primer can be prepared by cutting at an appropriate site of a circular DNA vector by restriction enzyme and then joining a 3'-end protruding primer sequence that is complementary to the part of mRNA. Also, in order to synthesize full-length cDNA, oligo dT (preferentially 30-70 nucleotides) may be joined at the 3' end. Especially, the double-stranded DNA primer possessing the oligo dT as a 3'-protruding end is preferable, for example, to efficiently prepare a full-length cDNA library. Also, in order to make it easy to recombine the cut cDNA into other vector, it is preferable to set up an 8-base recognition restriction enzyme site at the part of the double-stranded DNA. Furthermore, it is preferable to set up a replication origin at the part of the double-stranded DNA. As the replication origin, those that function in a prokaryotic cell such as *E. coli* or in eukaryotic cells such as yeast, insect cells, mammalian cells, plant cells and the like can be used. This enables us to replicate the obtained cDNA vector after introduction into these cells. Furthermore, it is preferable to set up a promoter, a splicing region, a poly(A) addition signal and the like at the part of the double-stranded DNA in order to express the cDNA in vitro by in vitro transcription/translation or in vivo by introducing into eukaryotic cells.

Figure 2:
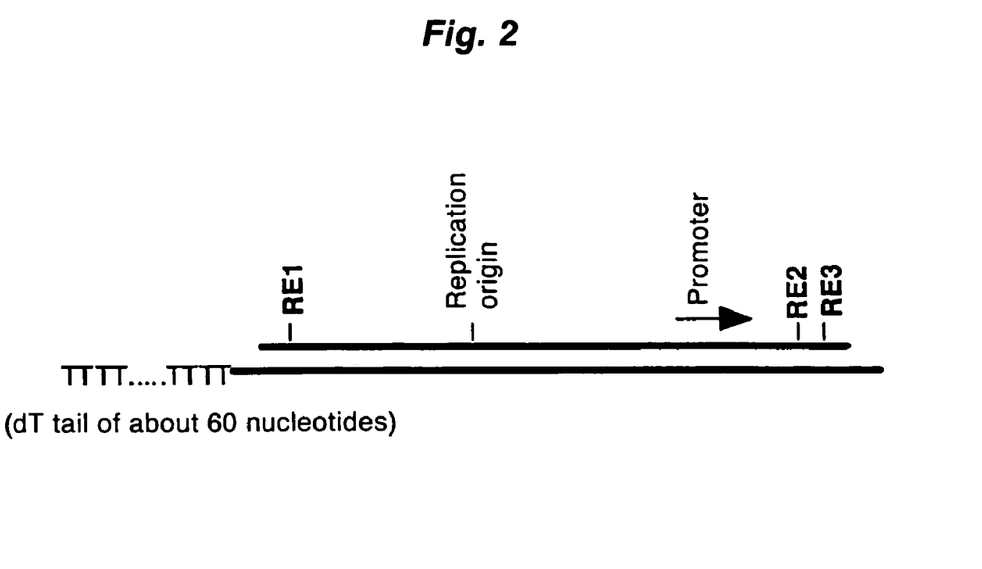
FIG. 2 is a view exemplifying the general structure of a vector primer of this invention.

These double-stranded DNA primers (the fifth invention) may be properly designed using an appropriate vector DNA as a starting material, or a known vector primer such as a pKA1 vector primer (one end possesses a 3'-protruding dT tail of about 60 nucleotides, and the other end is an EcoRV blunt end [Kato et al., Gene 150:243-250, 1994]) or the like can be used. The general structure of the double-stranded vector primer of this invention is shown in FIG. 2. This vector primer has 60+/−10 dTs as a primer sequence. The other terminal may be either a blunt end or a protruding end. It is preferable that the end of a primer side contains an 8-base recognition restriction enzyme site RE1 and that the other end has an 8-base recognition restriction enzyme site RE2 and a restriction enzyme site RE3 generating a 5'-protruding end or a blunt end. As an 8-base recognition restriction enzyme site, NotI, Sse83871, PacI, SwaI, SfiI, SgrAI, AscI, FseI, PmeI, SrfI or the like can be used. A vector primer pGCAP1 prepared in this invention has an AflII site (CTTAAG) as RE3. If the 3' end of the first-strand cDNA is joined to the 5'-protruding end of this AflII ( . . . CTTAA), in the case of "cap-consecutive cDNA", "dG" is added to the 5'-protruding end, resulting in generation of . . . CTTAAG . . . , that is, restoration of an AflII site. Thus, the "cap-consecutive cDNA" clones can be cut with AflII. Using this event, cutting with AflII can be used to determine whether or not cap-consecutive cDNA is synthesized. In addition, MunI(CTTAAG), XhoI(CTCGAG) or the like can be used as a restriction site that restores its recognition site by being added with "dG". The pGCAP10 vector primer prepared in this invention possesses NotI as RE1, SwaI as RE2, and EcoRI as RE3.

The third invention of this application is a "cDNA library" composed of a population of cDNA vectors that is the final product prepared by the method of the foregoing second invention. As shown in Examples later, the cDNA library is characterized by containing cap-consecutive cDNA clones at extremely high rates, more than 60%, preferentially more than 75%, further preferentially more than 90%, most preferentially more than 95%.

Accordingly, the cDNA library of this third invention enables us to isolate and analyze cap-consecutive cDNA at high rates without selecting them, because most of clones in the library are cap-consecutive cDNAs. For purpose of accuracy, the cap-consecutive cDNA can be correctly selected by the method of the forth invention of this application. Since the cap-consecutive cDNA synthesized by the method of the foregoing first and second inventions is characterized by the presence of "(dT)ndG" at the 5' end, we can identify the cap-consecutive cDNA by examining the presence of this "(dT)ndG" as an indicator without determining the entire nucleotide sequence of the cDNA. The presence of "(dT) ndG" can be examined using known methods for nucleotide sequencing. Since more than 90% of cap-consecutive cDNAs start with "dG", the presence of "dG" can be practically used as an indicator.

The sixth invention of this application is minimum reagents that are necessary for synthesizing cDNA using the method of this invention, that is, a cDNA synthesis reagent kit comprising a double-stranded DNA primer, reverse transcriptase and its reaction buffer solution, T4 RNA ligase and its reaction buffer solution, and model RNA possessing a cap. By using this kit, a cDNA library containing cap-consecutive cDNAs can be easily prepared from a given RNA mixture containing mRNA possessing a cap.

EXAMPLES

Hereunder, the invention of this application will be explained in more detail and specifically by showing Examples; however, the invention of this application is not intended to be limited to these Examples. Incidentally, basic procedures and enzymatic reactions related to DNA recombination followed the literature (Sambrook and Maniatis, in Molecular Cloning—A Laboratory Manual, Cold Spring Harbor Laboratory Press, New York, 1989). With regard to restriction enzymes and various modification enzymes, the ones manufactured by Takara Shuzo Co. Ltd. were used unless otherwise particularly stated. Composition of a buffer solution for each enzymatic reaction and reaction conditions followed the attached instruction.

Example 1 cDNA Synthesis Using Cap Analogue-attached RNA (1) Preparation of Cap Analogue-attached RNA A full-length cDNA clone of human elongation factor-1α (EF-1α), pHP00155 (Non-patent Document 6), was linearized by digesting with NotI, and then this was used as a template to prepare mRNA using an in vitro transcription kit (Ambion). By adding $m^7G(5')pppG(5)$ or $A(5')pppG(5)$ into the reaction solution as a cap analogue, model mRNA possessing "m⁷G" or "A" as a cap structure was obtained. In addition, by not adding the cap analogue, model mRNA without a cap structure was obtained. The 5'-terminal sequence of the in vitro transcription product is the sequence derived from the vector (5'-GGGAATTCGAGGA-3') followed by the 5'-terminal sequence of EF-1α (5'-CTTTTTCGCAA . . . ).

(2) Synthesis of the First-strand cDNA

The first-strand cDNA complementary to model mRNA was synthesized by mixing 0.3 µg of the forgoing model mRNA and 0.3 µg of a pKA1 vector primer (one end has a 3'-end protruding dT tail of about 60 nucleotides and the other end is an EcoRV blunt end) (Non-patent Document 6) in a reaction solution (50 mM Tris-HCl, pH8.3, 75 mM KCl, 3 mM MgCl₂, 5 mM DTF, 1.25 mM dNTP), annealing the model mRNA and the vector, adding 200 U of reverse transcriptase SuperScript™ II (Invitrogen) and 40 U of ribonuclease inhibitor (Takara Shuzo), and incubating at 42° C. for 1 hour. After the reaction solution was extracted with phenol, a conjugate of cap(+)mRNA/cDNA heteroduplex and a vector primer was recovered by ethanol precipitation and then dissolved in 20 µl of water.

(3) Decapping Reaction

The cap structure of mRNA was removed by mixing 20 µl of the cap(+)mRNA/cDNA heteroduplex solution in a reaction solution (50 mM sodium acetate, pH5.5, 5 mM EDTA, 10 mM 2-mercaptoethanol), adding 10 U of tobacco acid pyrophosphatase (Nippon Gene), and incubating at 37° C. for 30 minutes. After the reaction solution was extracted with phenol, a conjugate of decapped mRNA/cDNA heteroduplex and a vector primer was recovered by ethanol precipitation and then dissolved in 20 µl of water.

(4) Self-ligation

The end of the mRNA/cDNA heteroduplex and the EcoRV end of the vector primer were ligated and circularized (self-ligation reaction) by mixing 20 µl of either the cap(+)mRNA/cDNA heteroduplex solution obtained in the foregoing (2) or the decapped mRNA/cDNA heteroduplex solution obtained in the foregoing (3) with a reaction solution (50 mM Tris-HCl, pH7.5, 5 mM MgCl₂, 10 mM 2-mercaptoethanol, 0.5 mM ATP, 2 mM DTT), adding 120 U of T4 RNA ligase (Takara Shuzo), and incubating at 20° C. for 16 hours. After the reaction solution was extracted with phenol, a self-ligation product was recovered by ethanol precipitation and then dissolved in 20 µl of water.

(5) Replacement of RNA Strand with DNA Strand

A vector (cDNA vector) carrying an insert of a cDNA/cDNA duplex was obtained as a result of synthesizing the second-strand cDNA by replacing an RNA strand with a DNA strand; the replacement reaction was carried out by mixing 20 µl of the self-ligation product with a reaction solution (20 mM Tris-HCl, pH7.5, 4 mM MgCl₂, 10 mM (NH₄)₂SO₄, 100 mM KCl, 50 µg/ml BSA, 0.1 mM dNTP), adding 0.3 U of RNaseH (Takara Shuzo), 4 U of *E. coli* DNA polymerase I (Takara Shuzo), and 60 U of *E. coli* DNA ligase (Takara Shuzo), and incubating at 12° C. for 5 hours. After the reaction solution was extracted with phenol, the cDNA vector was recovered by ethanol precipitation and then dissolved in 40 µl of TE.

(6) Transformation of *E. coli*

Transformation was carried out using an electroporation method after mixing 1 µl of the cDNA vector solution with DH12S competent cells (Invitrogen). The electroporation was carried out using MicroPulser (BioRad). The obtained transformants were suspended in SOC medium, seeded on agar plates containing 100 µg/ml ampicillin, and incubated at 37° C. overnight. As a result, a library composed of about 10⁵-10⁶ *E. coli* transformants was obtained.

(7) Analysis of 5'-end nucleotide sequence of cDNA clones

Colonies grown on the agar plate were picked up, suspended in LB medium containing 100 µg/ml ampicillin, and incubated at 37° C. overnight. After cells were harvested from the culture medium by centrifugation, plasmid DNA was isolated and purified from the cells by the alkaline/SDS method. This plasmid was used as a template for a cycle sequencing reaction using a kit (BigDye Terminater v3.0, ABI), and the 5'-end nucleotide sequence of the cDNA was determined by a fluorescent DNA sequencer (ABI).

When model mRNA prepared using m⁷G(5')pppG(5) as a cap analogue was used as a template, 15 clones out of 20 clones carrying a cDNA insert contained cap-consecutive cDNA. With regard to these clones, extra "dG" (12 clones) or extra "dTdG" (1 clone) not existing in the model mRNA was added before the dG of the transcription start site. With regard to the remaining clones, 2 clones had no extra "dG" and 5 clones were cap-nonconsecutive cDNA starting with the middle of mRNA. Incidentally, decapping reaction did not influence the number of grown transformants, the ratio of cDNA starting with the cap site, and the addition of the extra "dG".

On the other hand, when model mRNA prepared using A(5')pppG(5) as a cap analogue was used as a template, 18 clones out of 24 clones carrying a cDNA insert contained cap-consecutive cDNA. With regard to these clones, extra "dA" (15 clones) or extra "dTdA" (1 clone) not existing in the model mRNA was added before the dG of the transcription start site. With regard to the remaining clones, 2 clones had no extra "dG" and 6 clones were cap-nonconsecutive cDNA starting with the middle of mRNA.

In addition, in both cases, the addition of extra "dG" or "dA" not existing in model mRNA was not observed in clones possessing cap-nonconsecutive cDNA.

Furthermore, when model mRNA without a cap structure was used as a template, 16 clones out of 19 clones carrying a cDNA insert contained the sequence starting with a transcription start site. Out of them, 14 clones did not possess an extra sequence before the dG of the transcription start site. However, with regard to 2 clones, extra "dT" not existing in the model mRNA was added before the dG of the transcription start site. With regard to the remaining clones, 3 clones were cap-nonconsecutive cDNA starting with the middle of mRNA.

These results suggest that, by using the method of this invention, the first-strand cDNA was added by a nucleotide "dC" complementary to a base "G" of a cap structure of mRNA used as a template, and the added 3'-end "dC" of the first-strand cDNA results in the addition of complementary "dG" to the second-strand cDNA. Furthermore, sometimes the complementary "dG" was followed by dT. Therefore the addition of "dG" or "dTdG" to the 5' end of the cDNA indicates that the cDNA is cap-consecutive cDNA.

(8) cDNA Synthesis Using Vector Primer with Protruding End

When self-ligation reaction was performed after synthesizing the first-strand cDNA and generating the 5'-protruding end by EcoRI cut of the vector primer, a cap-consecutive cDNA clone possessing "dG" at the 5' end was obtained as well as it was done using a vector primer with blunt-end EcoRV. Therefore, the restriction enzyme-cut end of the pKA1 vector primer can be not only a blunt end but also a 5'-protruding end. Furthermore, the use of the 5'-protruding end improved the efficiency of ligation and the number of clones composed of the cDNA library as compared with using the blunt end.

Example 2

Preparation of cDNA Library Using mRNA Derived from Cultured Cell HT-1080

Total RNA was prepared from human fibrosarcoma cell line HT-1080 (purchased from Dainippon Pharmaceutical Co. Ltd.) using the AGPC method (a kit from Nippon Gene). Poly(A)$^+$RNA was purified by binding to a biotinylated oligo (dT) primer (Promega), adding Sreptavidin MagneSphere Particles, and collecting by magnet. A cDNA library was prepared by synthesizing cDNA under the same conditions as described in Example 1 using 0.3 µg of poly(A)$^+$RNA and 0.3 µg of a pKA1 vector primer, and carrying out transformation of E. coli. As a result, a library containing about $10^5$-$10^6$ transformants was obtained. The libraries were prepared with or without decapping reaction, but there was no significant difference between analysis results of the two libraries. Thus, hereafter the results obtained without decapping reaction will be described.

The 5'-end nucleotide sequence of the cDNA was determined using a plasmid isolated from colonies that were randomly selected from the foregoing library. With regard to 191 clones carrying a cDNA insert whose sequence was determined, BLAST search was performed using GenBank nucleotide sequence database, showing that 189 clones of them had been registered in the database as a gene derived from mRNA. All of 178 clones accounting for 94% of total clones contained a coding region. Most abundant clones were those encoding ribosomal protein P1 and elongation factor 1-α and 5 clones each were obtained. The 5'-end nucleotide sequence of 5 clones each was all 5'-GCCCTTTCCT-CAGCTGCCGC . . . for ribosomal protein P1 and all 5'-GCTTTTTCGCAACGGGTTTG . . . for elongation factor 1-α. These sequences except for "dG" of the 5' end were identical with those of clones (Non-patent Document 6) obtained from the library prepared by the conventional method (the DNA-RNA chimera oligo capping method). By comparing the sequences with a genome sequence, it was shown that any "dG" of the 5' end did not exist in the genome sequence so that it was confirmed that the "dG" was added during cDNA synthesis. This was also confirmed by the data that 168 clones out of 178 clones containing a coding region started with "dG". Furthermore, 6 clones started with (dT)ndG (n=1-5). These clones may be produced by further addition of multiple "dT" to the added "dG".

Two clones had not yet been registered in the database as a gene derived from mRNA, but the sequences of these clones completely agreed with a part of a genome sequence and some sequences in EST database. Both of the sequences had the added "dG" not existing in the genome sequence. Therefore, these 2 clones are likely to be novel full-length cDNAs that have not been identified as a gene.

Eleven clones started with the middle of mRNA (cap-nonconsecutive cDNA). Three clones out of these cDNA clones started with "dG" of the 5' end, but these "dG" were derived from the corresponding mRNA, and clones possessing newly added "dG" were not observed.

From the above results, 180 clones out of 191 clones carrying a cDNA insert seem to be full-length (cap-consecutive cDNA) so that the full-length rate in total is calculated to be 94%. Since 3 clones out of 171 clones starting with "dG" of the 5' end were cap-nonconsecutive cDNA, in the case of this cDNA library, it can be guaranteed with probability of 98% that cDNA clones starting with "dG" of the 5' end and possessing a coding region are full-length cDNA. Especially, the clones starting with "dG" not existing in the genome sequence can be guaranteed to almost certainly be full-length cDNA.

Example 3

Preparation of cDNA Library Using Total RNA Derived from Cultured Cell Ht-1080

A cDNA library was prepared by synthesizing cDNA using 5 µg of total RNA prepared from human fibrosarcoma cell line HT-1080 and 0.3 µg of a vector primer under the same conditions as described in Example 1 (except for omitting decapping reaction), and transforming E. coli cells. As a result, a library containing about $10^5$ transformants was obtained.

The 5'-end partial sequences of cDNA clones in this library were analyzed as described in Example 2. With regard to 222 clones whose sequences could be determined, BLAST search using nucleotide sequence database of GenBank showed that 217 clones had been registered in the database as a gene derived from mRNA. Out of them, all of 209 clones accounting for 94% of total clones contained a coding region. Of these clones, 189 clones started with "dG". It should be noted that this library was prepared from total RNA but not from purified poly(A)$^+$RNA. Furthermore, a small amount (5 µg) of total RNA was used. Therefore, using this method, the purification process of poly(A)$^+$RNA can be omitted and a full-length cDNA library of high quality can be prepared from total RNA of several µg.

Example 4

Large-scale Sequencing Analysis of Full-length cDNA Library of Cultured Cell ARPE-19

A cDNA library was prepared by synthesizing cDNA using 2.5 µg of poly(A) $^+$RNA prepared from human retinal pigment epithelium cell line ARPE-19 (delivered from ATCC) and 0.7 µg of a vector primer under the same conditions as described in Example 1, and transforming E. coli cells. The 5'-end partial sequences of cDNA clones in this library were analyzed as described in Example 2. With regard to 3683 clones whose sequences could be determined, BLAST search using nucleotide sequence database of GenBank showed that 3662 clones had been registered in the database as a gene derived from mRNA. Out of them, 3474 clones accounting for 94% of total clones were full-length cDNA clones. With regard to these clones, 3069 clones started with "dG" or "(dT)ndG".

Example 5

Figure 3:
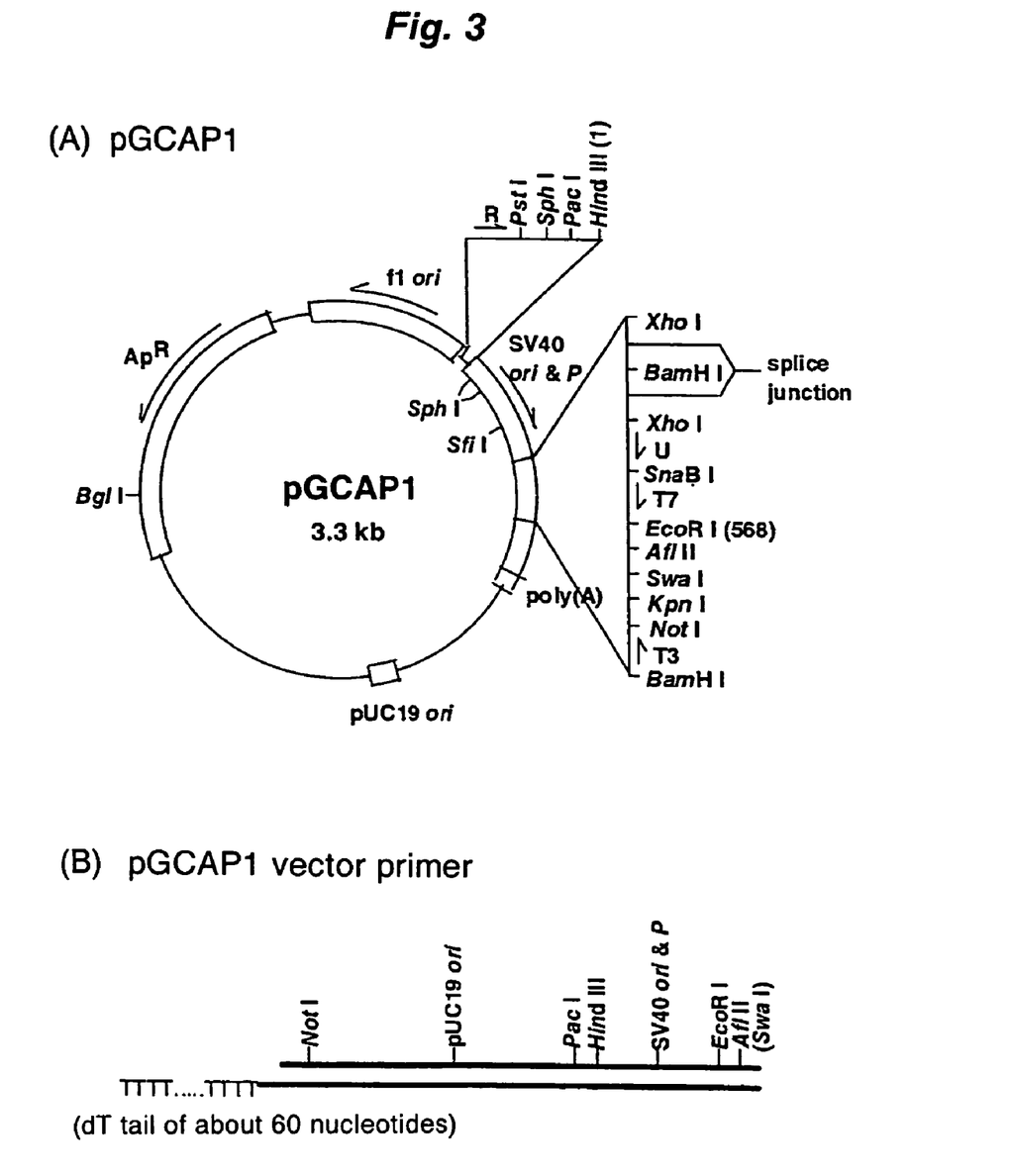
FIG. 3 is a view schematically showing the structures of pGCAP1 and a pGCAP1-derived vector primer of this invention.

Preparation of pGCAP1 Vector Primer pGCAP1 was prepared using a multifunctional cloning vector pKA1 (Non-patent Document 6) as a starting material. FIG. 3A shows a view of its structure and SEQ ID NO: 1 in a sequence list shows its entire nucleotide sequence. The differences from pKA1 are (1) changing its replication origin to pUC19-derived one, (2) adding PacI upstream of a restriction enzyme site HindIII in pKA1, (3) replacing an EcoRI-BstXI-EcoRV-KpnI site with an EcoRI-AflII-SwaI-KpnI site. The first nucleotide "A" in the sequence of SEQ ID NO: 1 corresponds to a HindIII site and the 568th does to an EcoRI site.

After 100 µg of pGCAPI was completely digested with 200 U of KpnI, a fragment was isolated by 0.8% agarose gel electrophoresis. By adding 375 U of terminal transferase (Takara Shuzo) to 70 µg of the obtained fragment in the presence of 20 µM dTTP and incubating at 37° C. for 30 minutes, a dT tail of about 60 nucleotides was added to the 3'-protruding end generated by KpnI digestion. Then the reaction product was digested with SwaI and the longer fragment was isolated by 0.8% agarose gel electrophoresis. This was used as a pGCAP1 vector primer (FIG. 3B).

Example 6

Preparation of cDNA Library Using pGCAP1 Vector Primer

A cDNA library was prepared by synthesizing cDNA under the same conditions as described in Example 3 using 5 µg of total RNA of human fibrosarcoma cell line HT-1080 and 0.3 µg of a pGCAP1 vector primer prepared in Example 5, and transforming *E. coli* cells. As a result, a library containing about $2 \times 10^5$ transformants was obtained. When the 5'-end partial sequences of the cDNA clones in this library were analyzed, it was shown that full-length cDNAs possessing "dG" at its 5' end were obtained and a full-length rate was 95% as in Example 3.

When a pKA1 vector primer is used, addition of one G to the EcoRV-cut end ( . . . GAT) results in generating . . . GATG . . . that contains a new initiation codon ATG. This is not a problem when the purpose is to know the sequence of the cap-consecutive cDNA, but the presence of extra ATG may have a bad effect on correct transcription/translation of the cDNA in the case of using this vector as an expression vector. By using a pGCAP1 vector primer, this kind of problem does not occur because the addition of one G to the SwaI-cut end ( . . . ATT) results in the generation of . . . ATTTG . . . that does not contain ATG.

Furthermore, when self-ligation was carried out after synthesizing the first-strand cDNA and generating a 5'-protruding end by cutting a vector primer with AflII, cap-consecutive cDNA possessing "dG" at its 5' end could be obtained as in the case of using a vector primer possessing blunt-end SwaI. When one G was added to the AflII-cut end ( . . . CTTAA), . . . CTTAAG . . . was generated, resulting in restoration of the AflII recognition site. As a result, cap-consecutive cDNA can be cut with AflII. Therefore, AflII digestion can be used to determine a cap-consecutive cDNA clone.

Example 7

Expression Profile Analysis of Cultured Cell ARPE-19 Full-length cDNA Library

A cDNA library was prepared from 5 µg of total RNA of human retinal pigment epithelium cell line ARPE-19 as described in Example 4, and then the 5'-end partial nucleotide sequences of the cDNA clones were analyzed. With regard to 3204 clones whose sequences could be determined, BLAST search using nucleotide sequence database of GenBank showed that 3038 clones accounting for 95% of total clones were full-length cDNA clones.

Examining the distribution of the insert size of these full-length cDNA clones showed that the clones contained inserts of a wide range of sizes from 0.1 kbp of the shortest one to 10 kbp of the longest one and that an average length was 1.94 kbp. The long-sized clones carrying a more than 3-kbp insert accounted for 16% of total clones.

These clones were classified into 1408 kinds of genes. Most abundant clone was glyceraldehydes-3-phosphate dehydrogenase cDNA whose content was 44 clones (1.4% of total clones). Only 235 kinds of cDNAs showed an expression level of more than 0.1%, that is, more than 2 clones each were obtained. On the other hand, 971 kinds of cDNAs (69% of total genes) were genes whose expression level was less than 0.03%, because only one clone each was obtained. Furthermore, some clones seem to be a novel gene clone of very low expression level, whose sequence agrees with the genome sequence but has not yet been registered in the database. As shown above, the obtained cDNA library was confirmed to be a low-redundant high-quality library containing a large number of genes of low expression level.

The results of above analysis suggest that the cDNA library prepared by the method of this invention contains full-length cDNA clones at high rates and truly reflects the expression level of mRNA expressed in cells because of no bias of gene length or its expression level. Therefore, this method is effective not only to obtain full-length cDNA clones but also to analyze the expression profile of genes expressed in the cells.

Example 8

Figure 4:
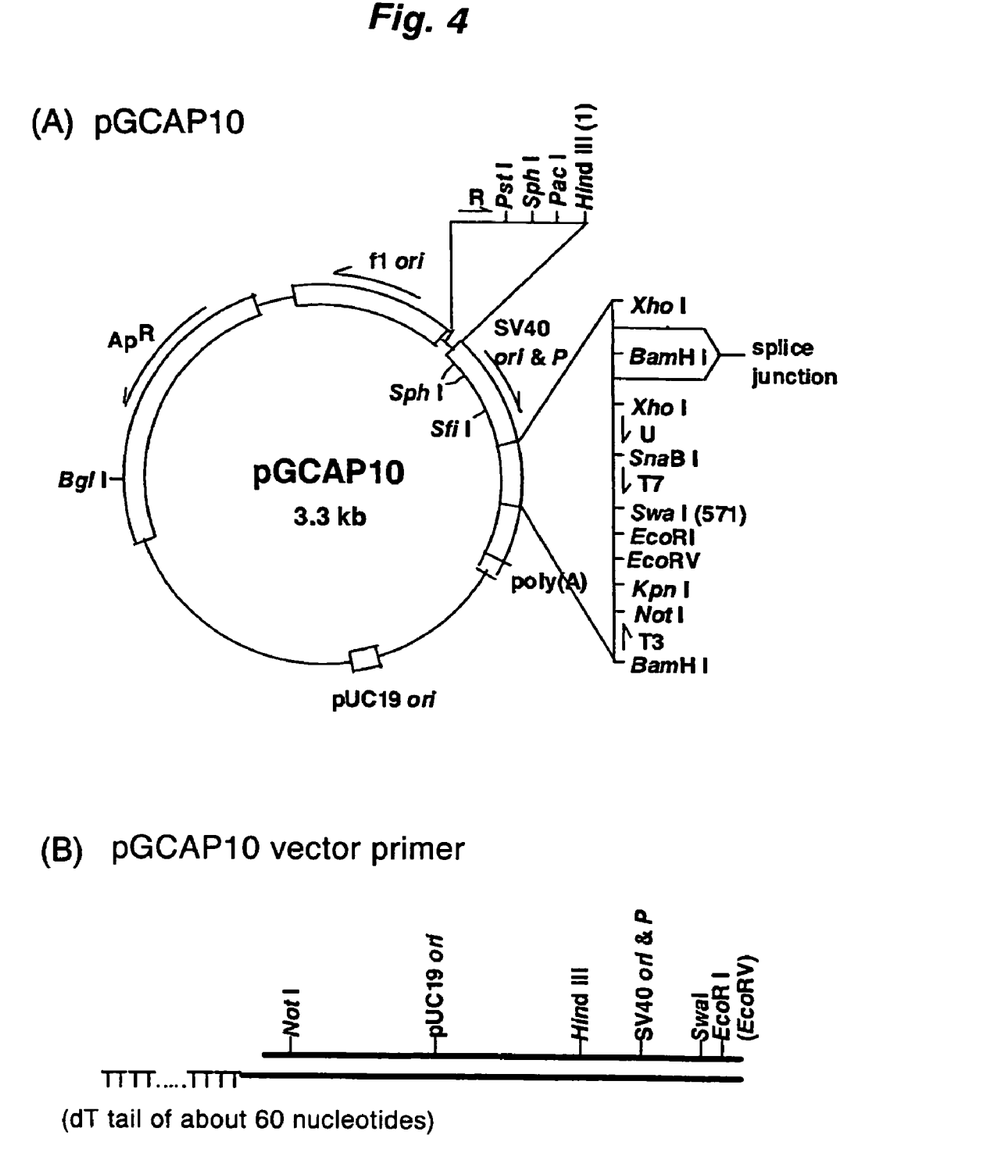
FIG. 4 is a view schematically showing the structures of pGCAP10 and a pGCAP10-derived vector primer of this invention.

Preparation of pGCAP10 Vector Primer and Preparation of cDNA Library Using This pGCAP10 was prepared using pGCAP1 as a starting material. FIG. 4A shows a view of the structure, and SEQ ID NO: 2 in the sequence list shows its entire nucleotide sequence. The difference from pGCAP1 is a SwaI-EcoRI-FseI-EcoRV-KpnI site produced by replacing an EcoRI-AflII-SwaI-KpnI site. As described in Example 5, a dT tail of about 60 nucleotides was added to the 3'-protruding end of KpnI in pGCAP10. After digesting the reaction product with EcoRV, a longer fragment was used as a pGCAP10 vector primer (FIG. 4B). Using 0.3 µg of this vector primer and 5 µg of total RNA of human fibrosarcoma cell line HT-1080, the first-strand cDNA was synthesized under the same conditions as described in Example 3, and then the end of the vector side was converted to a 5'-protruding end by EcoRI digestion. After self-ligation, the ligation product was used for transformation of *E. coli* cells by omitting the process replacing an mRNA strand with a DNA strand. As a result, a cDNA library containing about $10^6$ transformants was obtained. With regard to the cDNA clones in this library, analysis of the 5'-end partial sequence was carried out, showing that full-length cDNA added by "dG" at the 5' end was obtained and a full-length rate was 95% as in Example 3.

INDUSTRIAL APPLICABILITY

As described in detail above, by the invention of this application, full-length cDNAs that are guaranteed to possess a consecutive sequence starting with the nucleotide of a transcription start site can be synthesized from total RNA of one to several µg at high yield of more than 90% by small processes not using PCR. As a result, information on the primary structure encoded by the gene and information on the expression regulatory region controlling the expression of the gene can be robustly obtained so that this invention greatly contributes to not only the effective use of genome information but also the production of recombinant protein useful in medical fields and the like.

The invention claimed is:

1. A method for constructing a DNA vector having a cDNA synthesized from an mRNA, which method comprises the steps of:
   (i) annealing a double-stranded DNA primer and an mRNA mixture, wherein the double-stranded DNA primer consists of a first strand having a primer sequence and a second strand, and wherein the double-stranded DNA primer contains a replication origin or both a replication origin and a promoter for cDNA expression,
   (ii) preparing an mRNA/cDNA heteroduplex by synthesizing a first-strand cDNA primed with the primer sequence of the first strand of the double-stranded DNA primer using reverse transcriptase,
   (iii) circularizing the mRNA/cDNA heteroduplex by ligating the 3' end of the first strand cDNA to the 5' end of the first strand of the double-stranded DNA primer using T4 RNA ligase to form a circular mRNA/cDNA heteroduplex, and
   (iv) replacing the RNA in the mRNA/cDNA heteroduplex with a second-strand cDNA by synthesizing the second-strand cDNA with a DNA polymerase, thereby constructing the DNA vector having cDNA consisting of the first-strand cDNA and the second-strand cDNA.

2. The method of claim 1, wherein the mRNA is contained in a cell extract.

3. The method of claim 1, wherein the mRNA is synthesized by in vitro transcription.

4. The method of claim 1, wherein the primer sequence of the double-stranded DNA primer contains a sequence complementary to a partial sequence of the mRNA.

5. The method of claim 1, wherein the primer sequence of the double-stranded DNA primer contains an oligo dT complementary to a poly(A) sequence of the mRNA.

6. The method of claim 1, which comprises the following step between the step (ii) and the step (iii):
   (ii') generating a 5'-protruding end or a blunt end at the terminal of the double-stranded DNA primer by cutting the mRNA/cDNA heteroduplex using a restriction enzyme.

* * * * *